United States Patent
Ohta et al.

(10) Patent No.: US 6,395,717 B1
(45) Date of Patent: *May 28, 2002

(54) THERAPEUTIC DRUG FOR ENDOTOXIN BLOOD SYMPTOM AND MULTI-ORGAN FAILURE INDUCED THEREBY

(75) Inventors: Michio Ohta, Nagoya; Takaaki Hasegawa, Gifu; Masayuki Nadai; Yasuko Yoshida, both of Nagoya; Mitsuo Kawase, Chita; Tadahiko Inukai, Nagoya, all of (JP)

(73) Assignees: NGK Insulatirs, Ltd.; Biseiken Co., Ltd., both of (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/776,032
(22) PCT Filed: Dec. 12, 1995
(86) PCT No.: PCT/JP95/02541
§ 371 (c)(1), (2), (4) Date: Jan. 23, 1997
(87) PCT Pub. No.: WO96/37205
PCT Pub. Date: Nov. 28, 1996

(30) Foreign Application Priority Data

May 25, 1995 (JP) .............................. 7-126258

(51) Int. Cl.[7] ........................ A61K 31/726; A61P 31/00
(52) U.S. Cl. .............................. 514/54; 514/53; 514/61; 514/921
(58) Field of Search .............................. 514/25, 53, 54, 514/61, 62

(56) References Cited

U.S. PATENT DOCUMENTS

| 5,393,742 A | | 2/1995 | Ishii et al. ..................... 514/23 |
| 5,470,843 A | * | 11/1995 | Stahl et al. .................... 514/61 |
| 5,639,734 A | * | 6/1997 | Esko et al. .................... 514/25 |

FOREIGN PATENT DOCUMENTS

WO  95/05455  2/1995

OTHER PUBLICATIONS

Embase abstract, AN 80055974, Kovacs, I. B. et al., 1979.*
Connolly, D.T. et al, The Journal of Biological Chemistry, vol. 257, No. 2, pp. 939–945, Jan. 1982.*
Zacharias Dische and Ellen Borenfreund, J. Biol. Chem. 192, pp. 583–587 (1951) "A New Spectrophotometric Method for the Detection and Determination of Keto Sugars and Trioses".
E. K. Marshall, Jr., J. Biol. Chem. 122, pp. 263–273 (1937) "Determination of Sulfanilamide in Blood and Urine".
S. Norn et al.: "Carbohydrates inhibit the potentiating effect of bacteria, endotoxin and virus on basophil histamine release" Agents Actions, vol. 30, No. 1–2, Apr. 1990, pp. 53–56, XP002066937 *the whole document*.

(List continued on next page.)

Primary Examiner—Edward J. Webman
(74) Attorney, Agent, or Firm—Parkhurst & Wendel, L.L.P.

(57) ABSTRACT

Therapeutic drugs for endotoxin blood symptom and multi-organ failure induced by it is provided, which therapeutic during are composed of sialic acid its salt, polymers of sialic acid or a salt of the polymer as effective components and have high therapeutic effects for shock death and organ failure induced by endotoxin as well as high safety, and are effective for treatment of endotoxin-shock, and organ failure.

9 Claims, 3 Drawing Sheets

OTHER PUBLICATIONS

I.B. Kovacs et al.: "Inhibition by N–acetyl Neuraminic (Sialic) Acid of Platelet Aggregation Induced by Different Stimuli" Thromb. Haemostasis, vol. 42, No. 4, 1979, pp. 1187–1192, XP002066938 *the whole document*.

F.A. Drobniewski et al.: "Nonspecific Ionic Effects on the Cytolytic and Hemolytic Properties of *Bacillus thuringiensis* delta Endotoxins" Curr. Microbiol., vol. 15, No. 5, 1987, pp. 295–300, XP002066939 *abstract; table 1*.

* cited by examiner

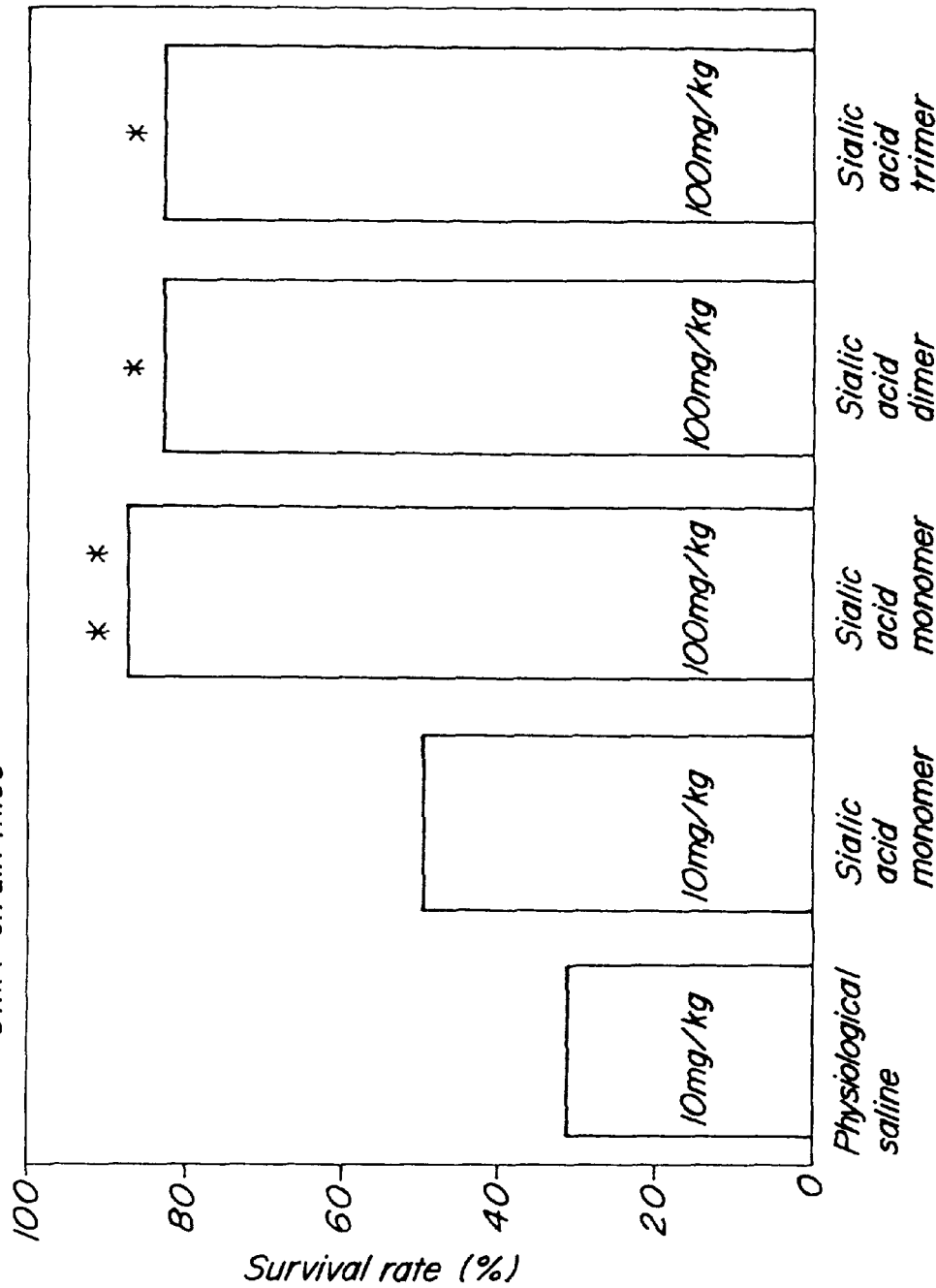

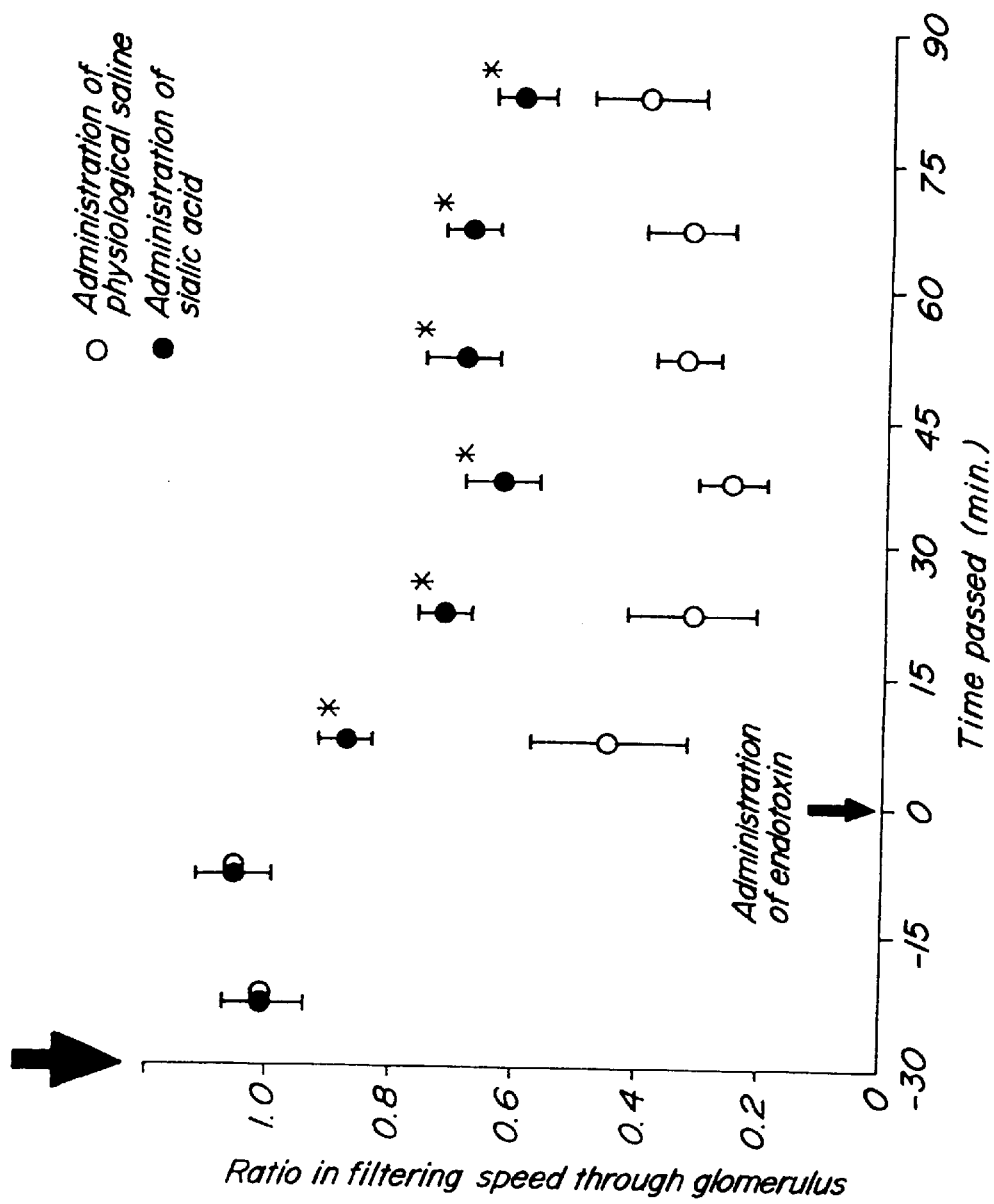

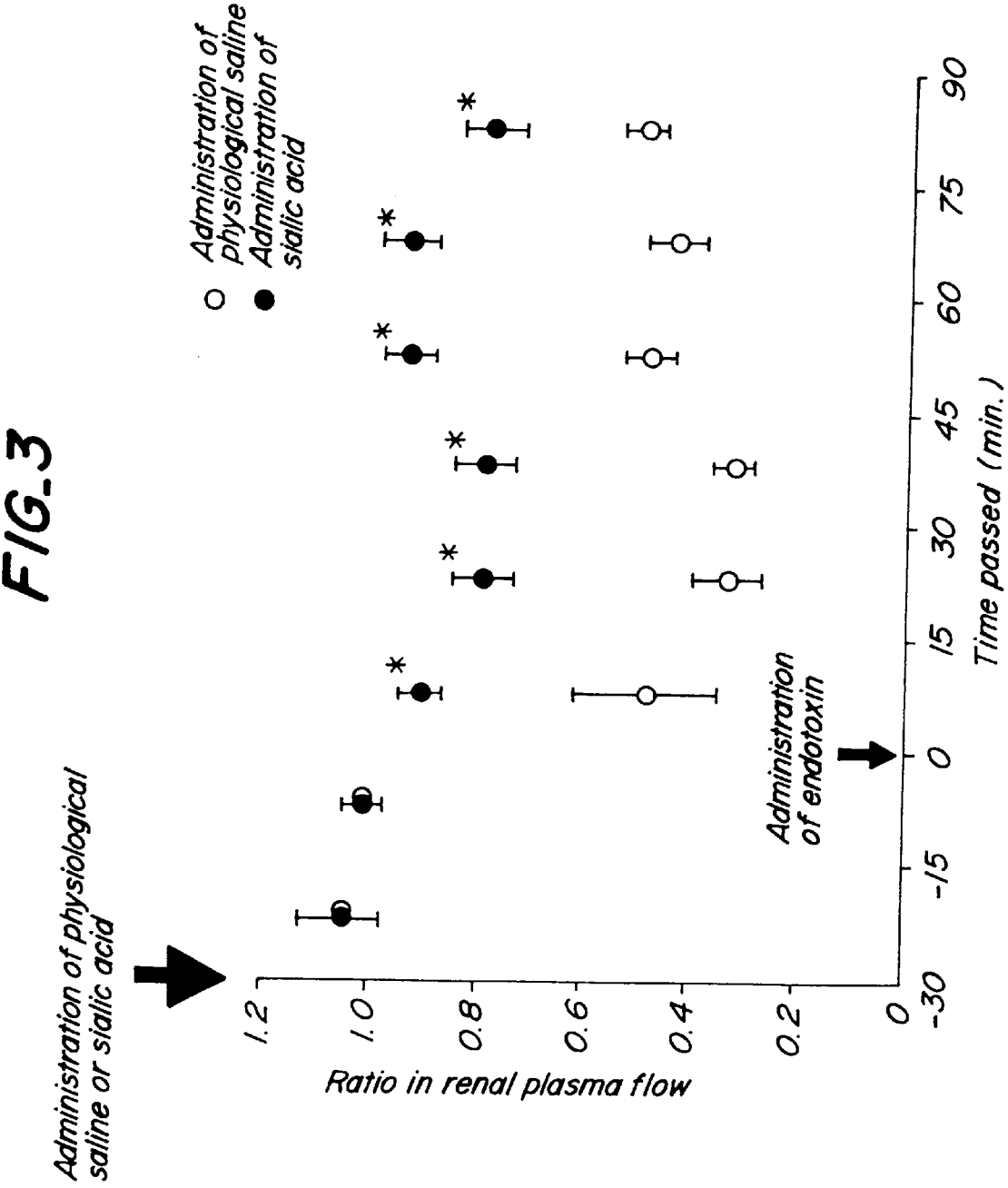

THERAPEUTIC DRUG FOR ENDOTOXIN BLOOD SYMPTOM AND MULTI-ORGAN FAILURE INDUCED THEREBY

The present invention relates to a therapeutic drug for an endotoxin blood symptom and multi-organ failure induced by it.

BACKGROUND ART

Endotoxins are lipopolysaccharides constituting cell membranes of Gram-negative bacteria, and their various physiological activities such as pyrexia, reduction in blood pressure, reduction in blood platelets, intravascular coagulation, promotion in capillary permeability, activation of complements, etc. are known. Therefore, if sepsis is induced through infection with Gram-negative bacteria, or if Gram-negative bacteria abnormally propagate in the large intestine, the concentration of the endotoxin in the blood increases so that the endotoxin blood symptom may appear. As various diseases caused by the endotoxin blood symptom, it is known that serious shock death may be induced or multi-organ failure may be provoked. As the multi-organ failure, hepatocirrhosis, fulminant hepatitis, acute renal failure, pulmonary failure, gastrointestinal bleeding, DIC (diffuse intravascular coagulation), etc. may be recited.

In order to prevent the endotoxin blood symptom, antibiotics have been formerly administrated for the purpose of suppressing the propagation of the Gram-negative bacteria as a source of generating the endotoxins. However, if a large amount of an antibiotic is administered, drug-resistant bacteria represented by MRSA come out to make the therapy more difficult, and the endotoxin blood symptom is aggravated by the release of the endotoxin from the Gram-negative bacteria killed by the antibiotic. Therefore, development of a therapeutic drug other than the antibiotics has been demanded.

From this purpose, antibodies against an endotoxin or a lipid A as a constituent component of the endotoxin has been developed. However, this measure have a drawback that since a neutralized effect differs depending upon the kinds of the Gram-negative bacteria, the therapeutic effect differs, too. Further, this measure has another drawback that since an antibody is produced against the endotoxin antibody by administrating a different kind of a protein, i.e., the antibody, side effects such as allergy, shock, etc. may occur in a continuous treatment.

DISCLOSURE OF THE INVENTION

The present invention has been made to solve the above-mentioned drawbacks of the prior art, and to provide a therapeutic drug for an endotoxin blood symptom and multi-organ failure induced by it, which therapeutic drug will not produce drug-resistant bacteria unlike in the use of antibiotics, can exhibit excellent therapeutic effects against various Gram-negatic bacteria, and enables the continuous treatment with high safety for human bodies.

In order to solve the above problems, the present inventors have noted diseases induced by the physiological activities of the endotoxins, and looked for medicines for reducing the appearance of such physiological activities. Then, the inventors looked for medicines capable of reducing the shock death with the endotoxins. As a result, they discovered that the shock death which might be caused by the administration of the endotoxin can be reduced with sialic acid or its polymer.

The present invention has been accomplished as mentioned above. A first invention is directed as its gist to a therapeutic drug composed of sialic acid or its salt as an effective ingredient and adapted for an endotoxin blood symptom and multi-organ failure induced by the endotoxin blood symptom. A second invention is directed as its as its gist to a therapeutic drug composed of a polymer of sialic acid or a salt of the polymer as an effective ingredient and adapted for an endotoxin blood symptom and multi-organ failure induced by the endotoxin blood symptom. As the polymer of sialic acid, polymers composed of two to thirteen sialic acid units may be used. The upper limit is posed upon the polymer composed of thirteen sialic acid units, because polymers composed of up to thirteen sialic acid units can be favorably produced. With respect to the polymers composed of two to thirteen sialic acid units and salts of such polymers, physiological effects similar to those of sialic acid and its salts can be expected. As the salts of sialic acid and its polymers, various pharmacologically acceptable salts may be used. As salts of a monomer of sialic acid, a sodium salt, a potassium salt, a calcium salt and a magnesium salt are ordinarily used. As salts of the polymers of sialic acid units, sodium salts are ordinarily used. "Sialic acid" used in the present specification means "N-acetylneuraminic acid".

As pharmaceutical preparations of the present invention, oral administration preparations such as tablets, capsules and powders, percutaneous absorption preparations such as suppository and vaginal suppository, and injections such as subcutaneous injection, intraperitoneal injections, and intravenous injections may be recited. Oral administration preparations are most preferable for preventing the diseases, and injections are most preferable for emergency use.

Oral administration preparations, percutaneous absorption preparations and injections can be formulated in ordinarily medicine-preparing methods. Formulating examples of an oral administration preparation and an injection are as follows.

1) Example of an Injection Preparation

After 50 g of sialic acid or its polymer is dissolved into 1000 ml of distilled water (free from pyrogen), the resulting solution is adjusted to pH 7.0 by using a solution of caustic soda, and filtered and sterilized by ordinary methods. Then, the sterilized filtrate is sealingly and aseptically charged into a 20 ml ample in the form of an injection.

2) Example of an Oral Administration Preparation

A capsulated preparation is produced by charging 280 mg of sialic acid or its polymer having passed a 60 mesh sieve into a No. 3 gelatin capsule.

A higher effect can be obtained in the administration of the pharmaceutical preparation of the present invention in the case that the preparation begins to be administrated to a infected person, particularly when he or she is turned to be infected with Gram-negative bacteria as compared with a case where the administration is begun after confirmation of any endotoxin blood symptom. Although an administrated dosage varies depending upon age, sex, disease degree, etc. of the patient, the dosage cannot be generally defined. However, when calculated as a sodium salt of sialic acid or its polymer contained in an injection, 1 to 2000 mg/Kg, preferably 10 to 500 mg/Kg, may be administrated to one adult per day. The number of administrations is appropriately one to six times per day. Venous instillation is an effective administration.

Since sialic acid is a substance which is much contained in terminals of saccharides present in surface layers of cells constituting the human body, and terminals of succharides present in the blood and the body fluid, the pharmaceutical preparations are medicines which give extremely small adverse effects upon the human body.

Sialic acid and its polymers used in the present invention may be either one of synthesized chemical products, enzymatically catalyzed synthesis products obtained by using sialic acid aldolase, cytosine monophosphate-N-acetylneuraminic acid (CMP-NANA) synthesis enzyme or CMP-NANA transferase and a hydrolyzed product of colominic acid obtained by decomposing colominic acid with an acid. But, they are not restrictive.

The endotoxin blood symptom and the multi-organ failure induced by it can be effectively medically treated with the therapeutic drug according to the present invention.

BRIEF EXPLANATION OF DRAWINGS

FIG. 1 is a graph illustrating effects of sialic acid upon endotoxin-shock in SMA-strain mice.

FIG. 2 is a graph illustrating changes in the ratio in filtering speed through glomerulus (Filtering speed through glomerulus at a given point of time/Filtering speed through glomerulus before administration of physiological saline or sialic acid).

FIG. 3 is graph illustrating changes in the ratio in renal plasma flow (Renal plasma flow at a given point of time/Renal plasma flow before administration of physiological saline or sialic acid).

BEST MODE OF CARRYING OUT THE INVENTION

The present invention will be explained below in more detail with reference to Examples.

1) Effect of Sialic Acid in Reduction of Endotoxin-shock

Tests were conducted with respect to endotoxin-sensitive, SMA-strain male mice (20 to 30 g) used: ① sixteen control mice, ② eight mice each administrated with sialic acid and ③ six mice each administrated with a polymer of sialic acid. ① With respect to the control mice, 0.1 ml/10 g of physiological saline was peritoneally administrated 30 minutes before the administration of an endotoxin. ② With respect to the mice administrated with sialic acid, a solution in which 100 mg of sialic acid was dissolved in 10 ml of physiological saline or a ten-times diluted solution thereof was peritoneally administrated to the mouse at a rate of 0.1 ml/10 g of the mouse (Dosage: 100 mg/Kg, 10 mg/Kg). ③ With respect to the mice administrated with the sialic acid polymer, a solution in which 100 mg of a dimer or a trimmer of sialic acid was dissolved in 10 ml of physiological saline or a ten-times was peritoneally administrated to the mouse at a rate of 0.1 ml/10 g (Dosage: 100 mg/Kg). Thirty minutes after the administration, a physiological saline solution of endotoxin (10 mg/ml) was peritoneally administrated to the mouse at a rate of 0.1 ml/mg (administrated amount: 100 mg/Kg). Then, the number of living mice 24 hours later was checked. Results thereof are shown in FIG. 1.

As shown in FIG. 1, ① with respect to the mice administrated with neither sialic acid nor its polymer, only five among sixteen (survival rate: 83.3%) survived. On the other hand, ② with respect to the mice administrated with 10 mg/Kg or 100 mg/Kg of sialic acid, four among eight (survival rate: 50%) and seven among eight (survival rate: 87.5%) survived, respectively. ③ with respect to the mice administrated with 100 mg/Kg of the dimmer or the trimmer of sialic acid, five among six (survival rate: 83.3%) survived. Significance was recognized at risk rates of not more than 1% (indicated by * * in FIG. 1) and not more than 5% (indicated by * in FIG. 1) with respect to the mice administered with 100 mg/Kg of sialic acid and its polymers, respectively. This means that sialic acid and its polymers control any step in provoking the death due to various physiological activities induced with endotoxin.

Now, it was made clear that sialic acid and its polymers have the function to reduce the endotoxin-shock. Therefore, presuming that sialic acid and its polymers have any therapeutic effect upon the multi-organ failure induced by the endotoxin blood symptom, such an effect was examined by adopting an experimental system of a renal failure induced by endotoxin as a typical disease thereof.

(2) Effect Upon Renal Failure

Into each of ten Whister-strain rats (8 to 9 week age) having undergone cannulation at the carotid canal and the bladder was intraveneously drip-infused a 4% manitol solution containing inulin (5 mg/ml) and paraaminohippuric acid (2.5 mg/ml) at a rate of 0.1144 ml/min. Thirty minutes thereafter, a physiological saline solution of sialic acid (5 ml/ml) was administered, at a rate of 0.2 ml/100 g (dosage: 10 mg/Kg), to each of the rats administered with sialic acid, whereas the same amount of physiological saline was rapidly interveneously injected to the control rats. Another thirty minutes thereafter, a physiological saline solution of endotoxin was interaveneously injected to the rats (dosage: 0.25 mg/Kg). Then, blood and urine were sampled over 90 minutes, and the concentrations of inulin and paraaminohippuric acid were measured. A kidney clearance was calculated according to the following formula. Urine was collected at an interval of 15 minutes after the administration of sialic acid or physiological saline (in FIG. 2, −15 to 0 minutes, 0 to 15 minutes, 15 to 30 minutes, 30 to 45 minutes and 45 to 60 minutes), and blood was sampled at a middle point of a time period during urine-collecting. The clearance values are shown at such middle points for the respective fractions.

Kidney clearance=Amount of the drug recovered in urine collected in the collecting time period÷Concentration of the drug in plasma at the middle point The concentration of inulin was measured by the Dishe & Borefreund's method (Z. Dishe and E. Borefreund, J. Biol. Chem., 192, 583–587 (1951)), and the concentration of paraaminohippuric acid was measured by the Marshall's method (E. K. Marshall, J. Biol. Chem., 122, 263–273 (1937)).

Results of the ratio in the filtering speed through glomerulus are shown in FIG. 2, and results of the ratio in renal plasma flow are in FIG. 3. In both the figures, the ordinate means the ratio in the filtering speed through glomerulus or the ratio in the renal plasma flow for 30 minutes between the intraveneous dip infusion of inulin and paraaminohippuric acid and the intraveneous injection of sialic acid or physiological saline.

As shown in FIGS. 2 and 3, with respect to the control rats administrated with no sialic acid, the ratio in the filtering speed through glomerulus and the ratio in the renal plasma flow rapidly dropped after the administration of endotoxin, and were dropped down to 40% of their respective normal values. As compared with this, with respect to each of the rats administered with sialic acid, the reduction in both the ratio in the filtering speed through glomerulus and the ratio in the renal plasma flow due to the administration of endotoxin was significantly prevented at a risk degree of 5% (shown by * in FIG. 3). With respect to the rats administered with sialic acid, the ratio in the filtering speed through glomerulus and the ratio in the renal plasma flow gradually decreased, without being rapidly dropped, after the administration of endotoxin, and decreased only by 30% and 20%, respectively, 30 minutes after the administration. Since no influence was observed for the ratio in the filtering speed through glomerulus and the ratio in the renal plasma flow with respect to the rats administered with sialic acid alone (−3 minutes to 0 minutes in the figures), sialic acid not completely but conspicuously prevented the renal failure induced by endotoxin.

Sialic acid used in each of Examples 1 and 2 was sialic acid obtained by decomposing columinic acid originatng from *Escherichia coli* with an acid, and separating and purifying the resultant, and sialic acid and having the purity of 98.5% and not more than 1% of analogues was used. The dimmer and the trimmer of sialic acid were separated and purified from an acid-decomposed liquid of *Escherichia coil* originated from columinic acid in the same way as in the case of sialic acid, and used in the form of a sodium salt. The purity was 99.5% for the sodium salt of the dimmer and 98.3% for that of the trimmer.

Acute Toxicity Test

An LD50 in the case of the intraveneous administration to a Wister-strain rats (male) was determined, according to which the sodium salts of both sialic acid and the trimmer (PH7) exhibited abnormality of 200 g/Kg.

Industrially Applicable Field

The therapeutic drugs composed of sialic acid and its polymers as effective ingredients have high therapeutic effects for shock death and organ failure induced by endotoxin as well as high safety, and are effective for treatment of endotoxin-shock, acute hepatic insufficiency, acute pulmonary insufficiency, DIC, etc. Further, the therapeutic drugs according to the present invention can exhibit high therapeutic effects without inducing medicine-resistive bacteria in the case of using antibiotics.

What is claimed is:

1. A therapeutic drug composition for treating endotoxin blood symptom and multi-organ failure induced by endotoxin comprising an endotoxin blood symptom and endotoxin induced multi-organ failure treating effective amount of a homopolymer of sialic acid or its salt and a pharmaceutically acceptable carrier therefor.

2. The therapeutic drug composition of claim 1, wherein said homopolymer of sialic acid contains 2 to 13 sialic acid units.

3. The therapeutic drug composition of claim 1, wherein said salt of said homopolymer of sialic acid is a sodium salt.

4. A method for treating endotoxin blood symptom and multi-organ failure induced by endotoxin comprising administering to a patient in need thereof an endotoxin blood symptom and endotoxin induced multi-organ failure treating effective amount of sialic acid, a salt thereof, a homopolymer of sialic acid, or a salt thereof.

5. The method of claim 4, wherein said salt of sialic acid is selected from the group consisting of a sodium salt, a potassium salt, a calcium salt, and a magnesium salt.

6. The method of claim 4, wherein said homopolymer of sialic acid contains 2 to 13 sialic acid units.

7. The method of claim 4, wherein said salt of said homopolymer of sialic acid is a sodium salt.

8. The method of claim 7, wherein said salt is administered by injection to an adult patient in an amount of 1 to 2000 mg/kg, based upon the patient's body weight.

9. The method of claim 5, wherein said salt is a sodium salt and is administered by injection to an adult patient in an amount of 1 to 2000 mg/kg, based upon the patient's body weight.

* * * * *